United States Patent [19]

McRae

[11] Patent Number: Plant 5,951

[45] Date of Patent: Apr. 21, 1987

[54] ASIATIC LILY NAMED ADELINA

[75] Inventor: Edward A. McRae, Boring, Oreg.

[73] Assignee: Melridge, Inc., Gresham, Oreg.

[21] Appl. No.: 710,614

[22] Filed: Mar. 11, 1985

[51] Int. Cl.[4] ..... A01H 5/00

[52] U.S. Cl. ..... Plt./68

[58] Field of Search ..... Plt./68

*Primary Examiner*—James R. Feyrer

*Attorney, Agent, or Firm*—John B. Lungmus

[57] ABSTRACT

A new variety of hybrid Asiatic lily having large compact racemes of flowers of large size and excellent form, an intense and unusual color pattern, and long persistence, both on the plant and as cut flowers. The flowers of this new plant are particularly characterized by their unusual combination of yellow and gold color tones, and by their very light maculation, a color pattern new in the upright Asiatic division of lilies. The plant itself is highly resistant to disease and shows high tolerance to virus, making it an excellent garden plant. Also, the bulbs may be precooled and forced for cut-flower production of flowers which are produced later than those of siblings similar in appearance, thereby extending the season of cut-flower production.

1 Drawing Figure

BACKGROUND OF THE INVENTION

My new variety of lily plant originated as a seedling selected from a group of seedlings grown at Sandy, Oreg., and resulting from my crossing of the species *Lilium wilsonii var, flavum* and "Connecticut King" as the pollen parent, this crossing having been done in the course of breeding efforts carried on by me since the year 1971 with the object of producing superior upright-flowering Asiatic lilies in shades of yellow and gold, suited to cut-flower production with a range of flowering times so as to extend the season of cut-flower production.

The flowers of my new lily plant are particularly characterized by large size, thick textured and very broad tepals having an unusual color pattern, each yellow tepal being flushed with gold adjacent its base end and having a very small amount of spotting adjacent each side of the nectaries. In addition, this new lily plant has, to a high degree, the desirable characteristics of hybrid vigor, great hardiness, and disease resistance, as observed in the area of Sandy, Oreg., with all of the desired characteristics of form, color, and habit. This clone is vigorous and a good grower and propagator.

This new variety of lily plant has been asexually reproduced by me and under my direction at Sandy, Oreg., and successive generations produced by bulb scale propagation and natural propagation from bulblets has demonstrated that the novel and distinctive characteristics of this new variety hold true from generation to generation and appear to be firmly fixed.

DESCRIPTION OF THE DRAWING

My new variety of Asiatic lily plant is illustrated by the accompanying photographic drawing, which shows an open bloom, hand painted to show the true coloration, illustrating the flower form, the tepal arrangement, and in particular the novel and distinctive yellow and gold color pattern, as well as its unusually broad tepals with their very light maculation.

DESCRIPTION OF THE NEW VARIETY

The following is a detailed description of my new variety of hybrid Asiatic lily with color designations according to The R.H.S Colour Chart, published by The Royal Horticultural Society of London, England.

THE PLANT

Origin: Seedling.

Parentage:

*Seed parent.*—*Lilium wilsonii var. 'flavum'* (unpatented).

*Pollen parent.*—"Connecticut King" (unpatented).

Classification:

*Botanic.*—Hybrid lily cultivar, Division 1-A of The Horticultural Classification of Lilies by The Royal Horticultural Society.

*Commercial.*—Upright Asiatic hybrid lily.

Form: Erect and tall, with a single stem.

Height: 120 to 170 cm. from bulbs 15 to 20 cm. in circumference.

Growth: Vigorous and sturdy.

Foliage:

*Quantity.*—Abundant.

*Leaf size.*—About 8 to 12 cm. long and 1.5 to 2 cm. wide.

*Leaf shape.*—Lanceolate with obtuse tip and entire margins.

*Texture.*—Leathery.

*Aspect.*—Glossy.

*Color.*—Both upper and bottom sides, medium to light green.

Bulbs:

*Size.*—Ranging up to 25 cm. in circumference for commercial use.

*Color.*—White.

THE BUD

Form: Long with ovate base and obtuse tip.

Size: About 7 to 9 cm. long just prior to opening.

Opening rate: The bud opens slowly at maturity, in response to light.

Color: Medium to deep yellow when the outer tepals first divide and when the tepals begin to unfurl.

Tepals:

*Color.*—Medium to deep yellow on both upper and bottom surfaces, the upper surface being flushed with gold adjacent the nectaries.

Peduncle:

*Length.*—About 7.5 to 10 cm., depending upon light levels.

*Color.*—Medium green.

THE FLOWER

Blooming habit: Annually, blooming once and profusely in the late Asiatic lily season. October-dug bulbs, properly precooled, planted under glass in February in western Oregon, with no supplementary lighting, flower in an average of about 80 to 85 days.

Size: Large; about 14 to 18 cm. in diameter.

Borne: In a compact raceme with about 6 to 8 flowers on a single stem, and the inflorescence may carry secondary buds.

Shape: Flat to slightly cup-shaped with the tepal tips lightly recurved, and the tepals being more broad in the mid-portion than the sepals.

Tepalage:

*Number.*—Six.

*Arrangement.*—Imbricated.

*Color.*—Yellow, RHS 12 A-B; each of the petals having a flush of Gold, RHS 21A, about 2 cm. wide and 2 cm. long above the nectary and along the midrib, the base end of the petals having a few small spots of deep magenta color on each side of the nectary furrows.

*Aspect.*—Shiny.

Pedicels:

*Length.*—About 4 to 6 cm. (The inflorescence carries some secondary buds on the shorter pedicels.)

Form.—Sturdy and upright.

*Color.*—Light green.

Fragrance: None.

Persistence: The flower is long lasting, both on the plant and as a cut flower, with the tepals staying on the stem about three weeks.

Disease resistance: The flower and plant are resistant to disease. Particularly resistant to Fusarium and Botrytis, as observed in the region of Sandy, Oreg.

REPRODUCTIVE ORGANS

046597217 Stamens:

*Number.*—Six.

*Arrangement.*—Typical of genus Lilium.

Anthers:

*Color.*—Greyed Gold, RHS 167A.

Filaments:

*Length.*—About 5 cm.

*Color.*—Ivory or yellow.

Pollen color: Same as anthers.

Pistils:

*Number.*—One.

Style length: About 5 cm.

Stigma color: Light plum to gold.

Characteristics of ovary: Typical of genus Lilium.

THE FRUIT

Fertility: The fruit is fertile.

Shape: Ovoid.

Color at maturity: Soft brown, sometimes overlaid with light plum.

This new variety of hybrid Asiatic lily most nearly resembles Connecticut King (unpatented) but the flower has much broader tepals each having a few small spots on each side of the nectary furrows at the base end. This new variety flowers later than does Connecticut King, thereby extending the cut-flower season.

Distinguishing Characteristics of Siblings From the Cross *Lilium Wilsonii* var. *flavum* x "Connecticut King"

| Cv | Days to Bloom | Buds | Maculation |
|---|---|---|---|
| Pollyanna Serial No. 710,427 | 80–85 | 5–8 | Heavy, large. |
| Joanna Serial No. 710,457 | 80 | 5–7 | Light |
| Adelina Serial No. 710,614 | 80–85 | 6–8 | Very few and small. Of deep magenta color. |
| Vanessa Serial No. 710,496 | 90–95 | 5–8 | Very light |
| Yolanda Serial No. 710,577 | 95–100 | 5–8 | Sparse and of deep magenta color. |
| Gold Medal (Half Sib) Serial No. 710,592 | 60–70 | 6–8 | Few, tiny |

| Cv | Other Notable Characteristics |
|---|---|
| Pollyanna Serial No. 710,427 | Relatively narrow, widely spaced tepals and sepals with very little marginal overlapping. Arrangement, hexagonal. |
| Joanna Serial No. 710,457 | Tepal-sepal angle 60°. Arrangement, generally imbricated. |
| Adelina Serial No. 710,614 | Tepals are large, thick textured, relatively broad, and with lightly recurved tips. Arrangement, imbricated. |
| Vanessa Serial No. 710,496 | Tepals have slightly recurved tips and inconspicuous maculation. Arrangement, uniformly imbricated. |
| Yolanda Serial No. 710,577 | Larger bulb, flower dished with tepal-sepal angle 60°, with lightly overlapping arrangement. |
| Gold Medal (Half Sib) Serial No. 710,592 | Very thick and broad tepals in 60° overlapping arrangement with sepals, Unusually long lasting flowers, bud blast resistant when forced, and attains large bulb size only in season. |

I claim:

1. A new and distinct variety of hybrid Asiatic lily, substantially as herein shown and described, characterized by the excellence of its flower form and, in particular, by its yellow and gold color pattern and light maculation, its vigorous growth and propagation character, its excellent flower form and substance, its versatility both as a garden plant and as a plant produced from precooled bulbs forced for cut-flower production, and its relatively late cut-flower season.

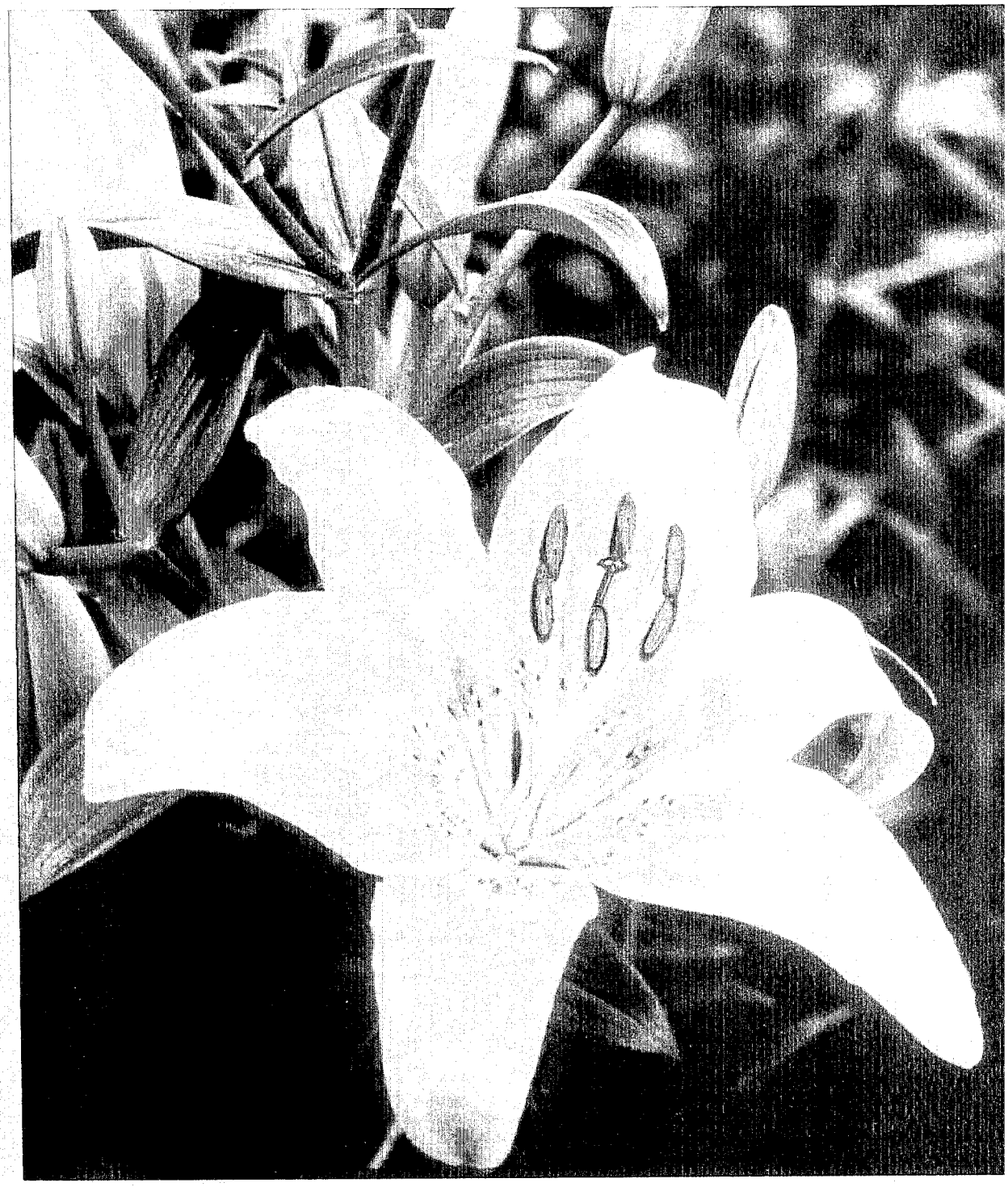

* * * * *